United States Patent [19]
Reiman

[11] Patent Number: 5,318,517
[45] Date of Patent: Jun. 7, 1994

[54] MULTIPLE LUMEN THORACOSTOMY CATHETER AND METHOD FOR ADMINISTERING ANESTHESIA

[76] Inventor: James A. Reiman, 7227 San Pedro Rd., Jacksonville, Fla. 32217

[21] Appl. No.: 859,668

[22] Filed: Mar. 30, 1992

[51] Int. Cl.⁵ ............................................. A61M 3/00
[52] U.S. Cl. ........................................ 604/43; 604/49; 128/207.14
[58] Field of Search .............. 604/93, 40, 42, 43–45, 604/29, 280, 244; 606/191, 192; 128/207.14, 203.13

[56] References Cited

U.S. PATENT DOCUMENTS

| | | | |
|---|---|---|---|
| 3,495,595 | 2/1970 | Soper | 604/28 |
| 3,929,126 | 12/1975 | Corsaut. | |
| 4,642,092 | 2/1987 | Moss | 604/43 |
| 4,842,583 | 6/1989 | Majlessi | 604/43 |
| 4,881,542 | 11/1989 | Schmidt et al. | 604/43 |
| 5,108,364 | 4/1992 | Takezawa et al. | 604/43 |
| 5,120,316 | 6/1992 | Morales et al. | 604/244 |
| 5,215,527 | 6/1993 | Beck et al. | 604/164 |

Primary Examiner—C. Fred Rosenbaum
Assistant Examiner—V. Alexander
Attorney, Agent, or Firm—James Creighton Wray

[57] ABSTRACT

The present invention provides an apparatus and a method for administering medicants, specifically anesthesia, to a catheterized patient. An administration tube is provided in longitudinal connection with an aspiration tube. The administration tube preferably has plural fenestrations provided along its length to administer anesthesia to the areas surrounding the catheter. The aspiration tube has at least one opening to aspire fluids from a patient. A preferred usage is for the interpleural space, wherein fluids are aspired through a series of aspiration apertures on the aspiration tube, and the surrounding tissues and intercostal nerves are anesthetized through the fenestrations to alleviate pain and discomfort commonly associated with catheters.

24 Claims, 3 Drawing Sheets

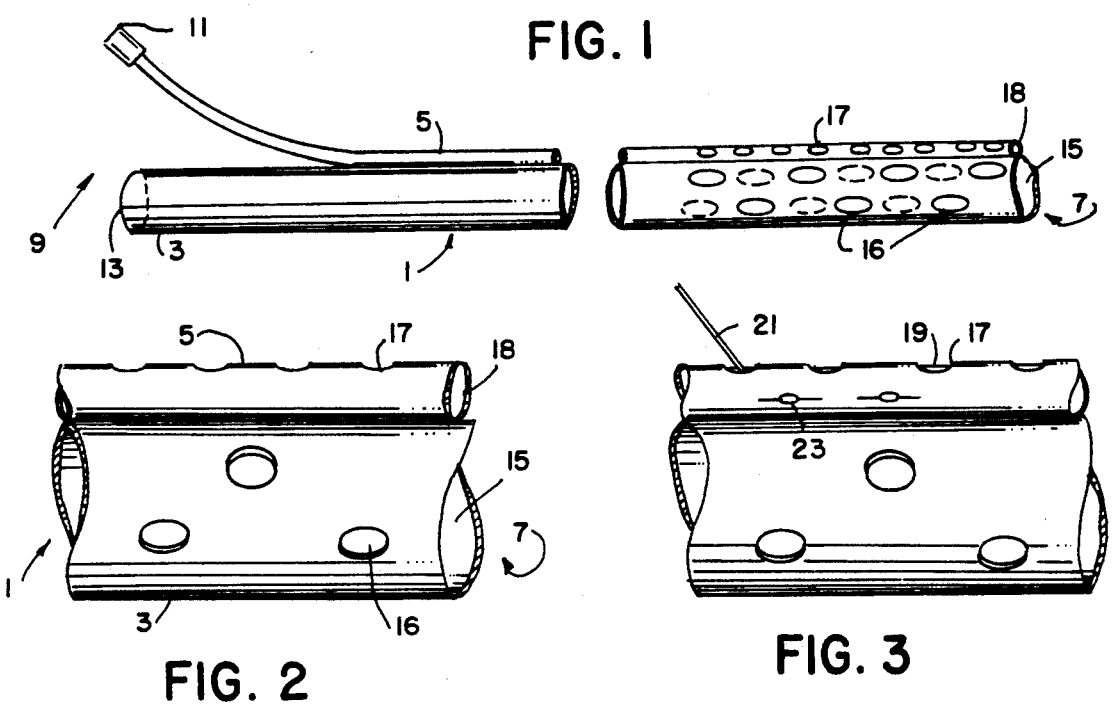
FIG. 1
FIG. 2
FIG. 3
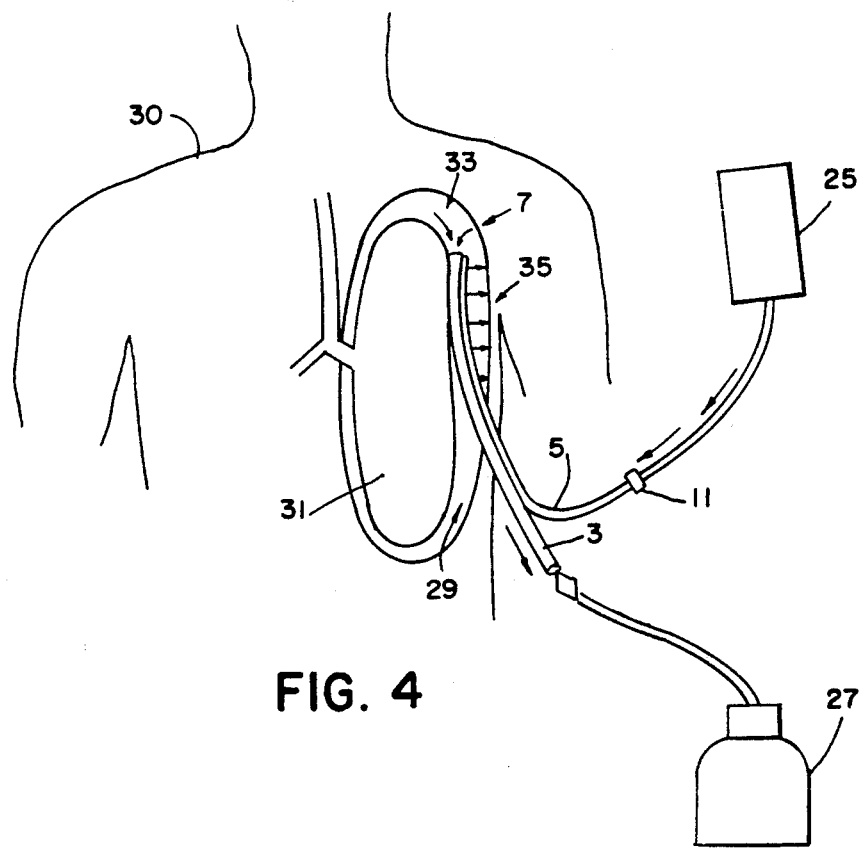
FIG. 4

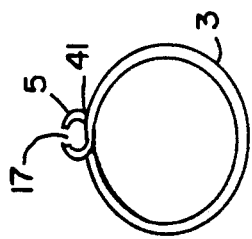
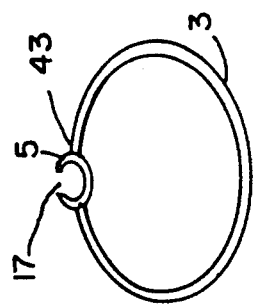
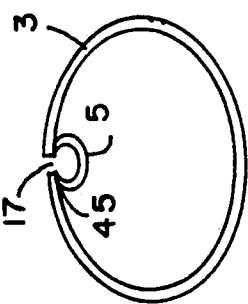
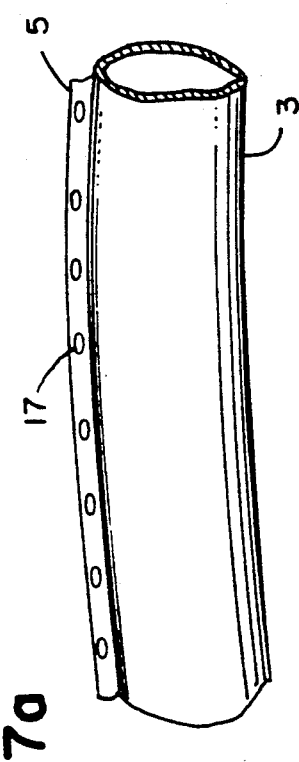
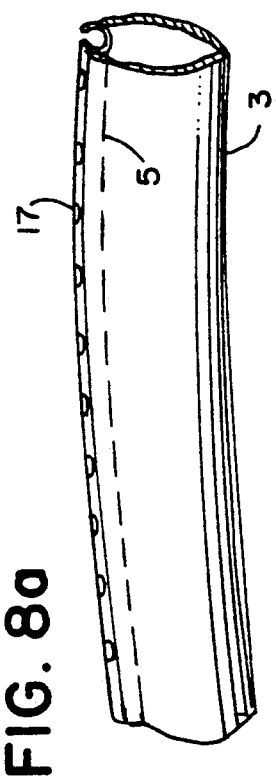
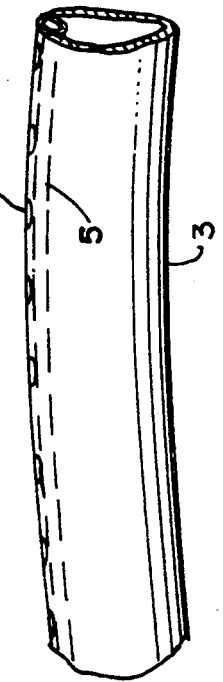
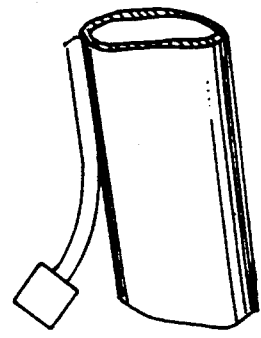
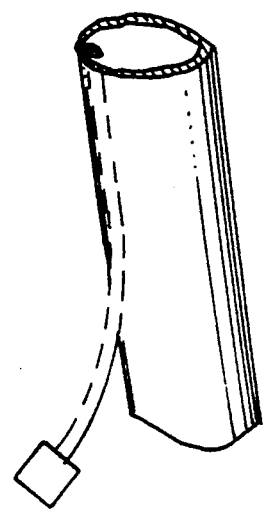

MULTIPLE LUMEN THORACOSTOMY CATHETER AND METHOD FOR ADMINISTERING ANESTHESIA

BACKGROUND OF THE INVENTION

The present invention relates to multiple lumen tubes for insertion into a patient. Specifically, the invention relates to evacuation of fluids from a patient's chest and problems associated therewith. More generally, the invention relates to anesthetizing areas adjacent to a catheter inserted into a patient.

The pleural space is a space between the lung and the chest wall. Intercostal nerves that provide sensation to the chest and abdomen lie in close proximity to the pleural space. In addition, nerve fibers that carry pain sensation lie within the lung tissue itself and are also close to the pleural space. Therefore, insertion of catheters into this space for evacuation of fluids or for other medical reasons causes extreme irritation and pain. It is therefore necessary to administer anesthetic to the patient. It is common to anesthetize a patient through oral or intravenous means. It is very difficult to localize these type of anesthetics, and various side effects are common. Installation of local anesthetics is preferable in such a case, thereby affecting only the nerve structures adjacent the catheters.

A major problem with installation of local anesthetics is the delivery of anesthetic to the appropriate nerves. One method involves placement of a thin flexible catheter into the pleural space using blind techniques. This results in a high incidence of misplacement into the lung and chest wall. Since the catheter cannot be directed into exact areas, large volumes of anesthetics must be used to fill the pleural spaces in order to block the appropriate nerves. This can result in high incidences of drug toxicity, leading to seizures and heart problems.

Many disease states and ailments of the lung require evacuation of air or liquids from the pleural space. These include trauma, cancer, pneumonia, infection and post-operative treatment. The most common technique for removal of these fluids involves placement of a large bore tube which provides suction or drainage. A major source of pain in these situations is the tube itself. The tube also lies adjacent to areas which generate pain, such as incisions or lesions. There is no known apparatus which simultaneously irrigates the pleural space while delivering anesthesia to alleviate associated pain and discomfort.

As with the pleural space, the use of catheters is common for treatment of ailments and post-operative treatment. It is also common for these inserted catheters to cause discomfort due to irritation of adjacent nerves. The present invention addresses the problems associated with thoracostomy tubes, as well as general problems with present catheters.

SUMMARY OF THE INVENTION

The present invention provides local anesthetics to exact areas of painful stimuli in a catheterized patient. The maximum amount of anesthesia can be obtained using this method without reaching a volume which would result in toxicity. The present invention places a second tube colinearly with a drainage tube, wherein the second tube provides an avenue for anesthesia to be delivered to exact areas of painful stimuli. Further, the second tube also allows for administration of other medicants to the areas along the catheter.

Catheters are an irritant which may cause discomfort. The present invention provides an evacuation or drainage catheter with at least one colinearly placed administration tube to provide an avenue for injection of anesthetics or other medicants. This allows for alleviation of discomfort and provides other necessary treatments while maintaining the integrity and sterility of the original catheter. Specifically, the present invention has a preferred embodiment which relates to treatment of the lungs, involving drainage of the interpleural space. It is necessary to alleviate pressure and aspire fluid, both liquid and gaseous, when administering post-operative or corrective treatment. This involves the use of a thoracostomy tube or catheter. It is typical for such catheters to cause extreme discomfort, particularly due to the placement and proximity to the nerves of the chest. The present invention provides an administration tube which runs colinearly with and is attached to an aspiration or pressure-relieving tube. As well as providing an avenue for anesthetics, medicants such as chemotherapy and saline may be provided without jeopardizing the sterility or integrity of the original catheter. Specifically, the anesthetics may be delivered to provide post-operative or post-traumatic pain relief by way of anesthetizing intercostal nerves.

The present invention in its preferred embodiment is a semi-stiff tube of suitable material, typically PVC tubing used in catheter construction, but alternatively stiffer or more elastic material as called for by the needs of the patient and professional. The invention is preferably at least a double lumen tube with a larger bore tube and a colinearly placed smaller bore tube. The larger bore tube functions by providing a means of drainage through suction or gravity. The smaller bore tube provides a means of administration of medicants, while the larger tube remains dedicated to drainage.

In its preferred embodiment, the tube is of PVC or clear plastic. However, other suitable materials may be used for the desired stiffness for maneuverability or strength.

The larger bore tube is of a diameter appropriate for the type of fluid being drained.

Total length of the colinearly placed tubes is important only with regard to placement of drainage holes on the larger bore tube and/or fenestrations provided on the smaller bore tube.

There should be at least one drainage hole placed on the larger bore tube, specifically at the inserted end. However, in a preferred embodiment, at least one hole is placed in a circumferential pattern on a section of the tube inserted into the body.

The preferred embodiment of the invention places at least one small bore tube attached in a colinear fashion with the large bore tube. Preferred embodiments include attaching the smaller bore tube to the larger bore tube exteriorly, forming the smaller bore tube within the wall of the larger bore tube, or connecting the smaller bore tube within the larger bore tube.

In all of the embodiments, the small bore tube has at least one fenestration provided proximal the inserted end. Plural fenestrations would preferably be spaced apertures for administering medicants to the appropriate anatomical structures. In the case of anesthetizing the interpleural cavity, the fenestrations may be provided in a fashion so as to affect the intercostal nerves. The spacing of the fenestrations alternatively can be standard to affect all areas proximal the inserted catheter. All open fenestrations should be inside of the body so as to prevent leakage, and should be communicable with the exterior of the catheter so as to affect surrounding body tissues. In a preferred embodiment, the fenestrations are provided with rupturable membranes which can be selectively ruptured by the medical personnel to selectively affect areas of tissue along the running length of the catheter. Other apertures such as slits are within the scope of the invention. Branch administration tubes or multiple dedicated administration tubes are preferred embodiments of the present catheter.

The proximal or exterior end of the catheter should have a connector for connection of the smaller bore administration tube to the appropriate administration device. In one embodiment, a screw-type thread connector is preferable, but other intravenous connection means, hypodermic insertion membranes and other connections are within the scope of the invention. An aspiration or large bore tube connector is provided on the larger bore tube for connection to aspiration, suction or drainage means.

While the present invention has been described in detail for use in the interpleural for a patient, it is within the scope of the invention to include all catheter applications where application of anesthesia and/or other medicants may be necessary to improve a patient's health. Minor alterations specific to the area to be catheterized can be provided, while still allowing the fenestrated tube application with an aspiration tube. Further, it is not beyond the scope of the invention to vary the respective sizes of the colinear administration and aspiration tubes. For some uses, it may be necessary to have a larger administration tube than aspiration tube. Further, the colinear tubes may be constructed of different materials to provide varying stiffness and clarity. Also, multiple connectors for the administration tube may be provided for administering medicants without disconnecting the anesthesia. The aspiration tube may in some circumstances be used for administration of large quantities of fluid, or may lie idle while the administration tube continues to provide medication to the patient.

The present invention finds ready usage in a variety of other medical applications, and is not constrained to use with the interpleural space. All catheters are painful irritants, and the present multiple lumen tube is an inexpensive device and means for alleviating discomfort.

In its preferred embodiment, the multiple lumen thoracostomy catheter comprises an aspiration tube for aspiring fluids from a patient and an administration tube longitudinally connected to the aspiration tube for administering medicants to a patient. The connected tubes form a catheter having an insertion end and a connection end. At least one administration fenestration is provided on the administration tube proximal the insertion end, and at least one aspiration aperture is provided on the aspiration tube proximal the insertion end.

Preferably, the administration tube has a smaller diameter than the aspiration tube. Both tubes are made of a flexible yet semi-stiff material, such as plastic or PVC material.

The administration fenestrations can be plural spaced apertures longitudinally placed on the administration tube proximal the insertion end.

In one embodiment, membranes are provided over the fenestrations. Selective puncturing of the membranes allows for selective communication of the administration tube to given areas in the patient's body.

The administration tube can be longitudinally connected to the exterior of the aspiration tube, within the wall of the aspiration tube, or within the interior of the aspiration tube.

The aspiration tube preferably has a first aspiration opening at the insertion end, and at least one aspiration aperture is in the wall of the aspiration tube proximal the insertion end for aspiring fluids at the insertion end and along a length of the inserted tube, respectively. The aspiration apertures in the wall of the aspiration tube can be a pattern or a series of openings extending from the insertion end within the patient.

In a preferred usage, the instrument is a thoracostomy catheter, wherein fluids in interpleural spaces are aspired through the aspiration tube and medicants are injected to the areas surrounding the catheter through fenestrations provided in the administration tube.

The administration tube can have one or more branch tubes extending from the administration tube towards the insertion end of the catheter. The branch tubes incorporate application fenestrations for delivery of medicants with the administration tube and can be connected to the same administration connector or be dedicated tubes with separate connectors.

The present invention also provides a method for administering medicants to a catheterized patient. An administration tube used in longitudinal connection to an aspiration catheter and provided with longitudinally spaced fenestrations supplies medicants to the patient. The medicants are released through the fenestrations along a length of the administration tube connected to the catheter, thus localizing the medicant to the area around the catheter.

The medicants are preferably anesthesia, but can be others such as chemotherapy.

When using anesthesia, the fenestrations can be selectively spaced and areas of nerve concentrations selectively sedated.

The fenestrations can also be provided as apertures with opening sizes chosen for regulating amounts of medicants to be administered to given areas around an aperture.

These and further and other objects and features of the invention are apparent in the disclosure, which includes the above and ongoing written specification, with the claims and the drawings.

BRIEF DESCRIPTION OF THE DRAWINGS

FIG. 1 is a side view of the basic thoracostomy tube.

FIGS. 2 and 3 show detail of the fenestrations.

FIG. 4 is a view of the tube when inserted into the interpleural space.

FIGS. 7a and 7b are side and cross-sectional views of a preferred embodiment with an administration tube longitudinally connected exteriorly to the aspiration tube.

FIGS. 8a and 8b are side and cross-sectional views of a preferred embodiment, wherein the administration tube is connected within the wall of the aspiration tube.

FIGS. 9a and 9b are side and cross-sectional views of the administration tube connected interiorly with fenestrations communicable exteriorly through the wall of the aspiration tube.

DETAILED DESCRIPTION OF THE DRAWINGS

Figure 5:
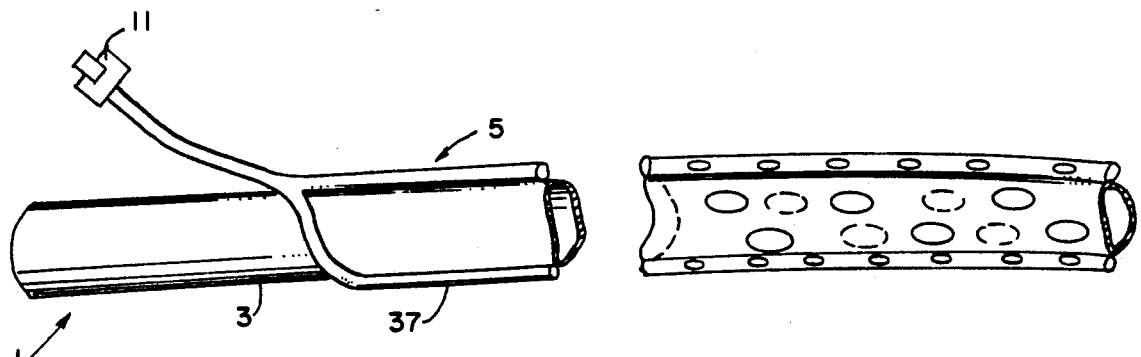
FIG. 5 is a side view of the invention showing addition of administration branch tubes.

The preferred multiple lumen thoracostomy catheter, generally indicated by the numeral 1 in FIG. 1, incorporates an aspiration tube 3 and at least one longitudinally connected administration tube 5. The catheter 1 has an insertion end 7 and a connection end 9. At the connection end 9 the administration tube 5 has an administration connection means 11 for connection to an anesthesia or other medicant administration device. The aspiration tube 3 has an aspiration connection end 13 at the catheter connection end 9 for connection to suction or other aspiration or drainage means. The aspiration tube 3 further has at least one aspiration aperture 15, preferably at the insertion end. In a preferred embodiment, intermediate aspiration apertures 16 are provided proximal the insertion end, preferably in a spaced or patterned relationship, for evacuating fluids along a length of the aspiration tube. The administration tube 5 is preferably provided with at least one fenestration 17 for administering anesthesia or other medicants from the administration connection 11 through the hollow administration tube 5 through the fenestration 17 to the patient proximal the inserted catheter. It is preferable that the administration tube 5 has a series of fenestrations, as shown in FIG. 1, to supply these fluids along a length of the catheter 1. An end fenestration 18 can be provided.

It is preferable that both the administration and aspiration tubes be hollow structures made of a flexible, semi-stiff material such as plastic or PVC material. These products are inexpensively manufactured and can have varying stiffness or malleability according to the needs of the patient. The tubes are preferably connected longitudinally by heating, stamping, sonic welding, gluing or other techniques typically utilized in adhering such material. The tubes may be of the same material, or made of materials of varying stiffness or clarity, depending on the situation.

In a preferred embodiment, the aspiration tube is a first tube having a larger bore than the second, longitudinally connected administration tube. The length of the connected tubes is related to the depth of insertion needed, whereby the fenestrations and apertures would preferably be kept within the body of a patient. Varying sizes may be specified during manufacture, or one size could be used and tailored by the medical professional through removing a given length of the insertion end. A standard size would have a given length of fenestrations and apertures which would fit within an average adult, but the same apparatus could be used on a child by cutting off a given length at the end 7 of the catheter 1.

FIG. 2 shows a detail of the catheter 1 proximal the insertion end 7. Both tubes are hollow structures. The intermediate aspiration apertures 16 are provided in a fashion so as to maximize aspiration of a cavity, or to regulate the amount of fluid to be aspirated. The series pattern in FIG. 2 is typical of a pattern which may be provided near the end aspiration opening 15 at the insertion end 7. The fenestrations 17 on the administration tube 5 are, in a preferred embodiment, spaced openings provided to administer anesthesia or medicants evenly along a length of the tube.

In FIG. 3, variations to the fenestrations are shown. Along a length of an inserted catheter there may be concentrations of nerves which the physician may want to selectively effect. Further, one area of a patient may require higher doses of medicants than other areas, such as administration of chemotherapy locally to a diseased area. Also, the physician may want to regulate the amount of medicants or anesthesia to be administered along a length of the tube. Therefore, the fenestrations 17 can be provided with rupturable membranes 19 which seal the length of the tube from exterior communication. Insertion of a needle 21 or similar instrument through the membrane allows communication from the administration tube to the patient to selectively affect areas around the catheter. Other fenestrations, such as the slit fenestration 23 in FIG. 3, can be provided and are within the scope of the present invention.

In a preferred embodiment as shown in FIG. 4, the catheter 1 is preferably a thoracostomy catheter for insertion into the interpleural space 29 of a patient 30. The interpleural space 29 is the space between the lung 31 and the surrounding membrane. Nerve structures within the pleural space and lung itself are extremely sensitive, and insertion of a catheter into this space for evacuation of fluids causes extreme irritation and pain. The object of the present invention is to evacuate fluids, as shown by arrows 33, from the pleural space 29 using suction or other techniques 27, while at the same time anesthetizing the patient through providing anesthesia, as shown by arrows 35, along a length of the inserted catheter 7. The administration tube 5 is connected at connector 11 to an IV or other administration device 25.

The present invention has all the advantages of previous evacuation catheters, but allows for localized administration of anesthesia and other medicants in specific amounts along the length of the tube while maintaining sterility.

In a preferred embodiment, the administration tube 5 may have at least one branch tube 37, also connected to the aspiration tube 3. Branch tubes vary the flow or area of coverage of the administration tubes. The branch tubes may be of varying lengths, numbers or sizes of fenestrations, or separate dedicated administration tubes (not shown) with their own connection devices 11 may be provided to administer different medicants or anesthesias simultaneously.

Figure 6:
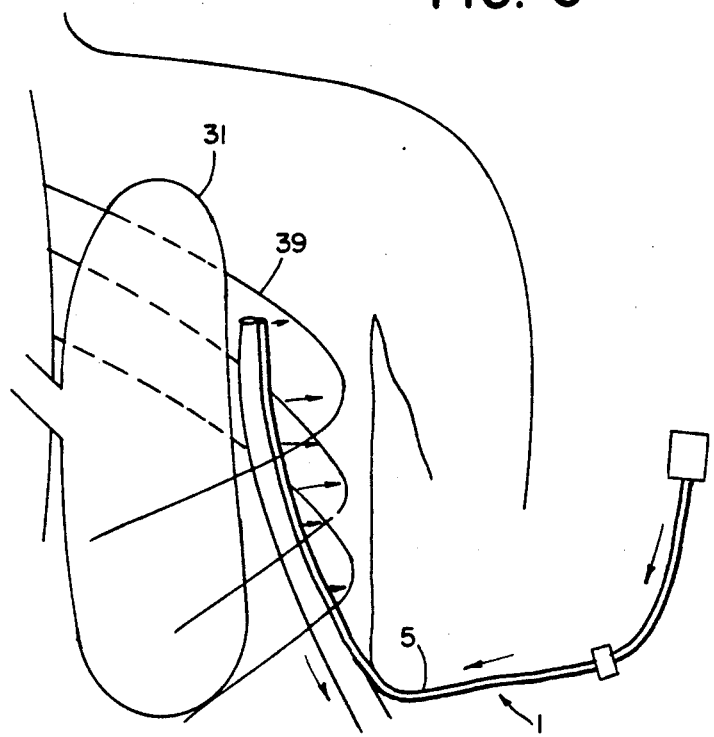
FIG. 6 is a view of the inserted tube anesthetizing the nerves.

In FIG. 6, a primary use of a preferred embodiment of the present catheter 1 is shown. The intercostal nerves 39 radiate proximate the interpleural space and are spaced and have different nerve levels. Previous methods have anesthetized the whole interpleural space, thus administering large amounts of anesthesia. This can lead to drug toxicity. With the present invention, the fenestrations can selectively affect areas of nerve concentrations and/or can affect only the areas proximal the catheter, thereby reducing, if not eliminating, the threat of drug toxicity. This concept is easily expanded to include other uses for catheters, because catheters are typically irritants which are undesirable at best to patients. The present catheter 1 provides side-by-side administration tube and evacuation tube to selectively affect areas of a patient around an inserted catheter. As well as anesthesia, medicants such as chemotherapy could be administered to damaged or diseased areas, either selectively or along the entire length of the tube.

In an alternate embodiment, the aspiration tube may be used for administration of fluids such as saline for flushing, and then reconnected to suction to drain the administered fluids.

Varying the relational sizes of the administration and aspiration tubes is not beyond the scope of this invention.

As shown in FIGS. 7a and 7b, a preferred embodiment provides the administration tube 5 with an exterior connection 41 to the aspiration tube 3.

Alternatively, as shown in FIGS. 8a and 8b and further in FIGS. 9a and 9b, the administration tube may be provided within the wall of the aspiration tube or connected interiorly. In FIG. 8b, interior wall connection means 43 provides the administration tube 5 within the wall of the aspiration tube 3. In FIG. 9b, the administration tube 5 is connected to the interior of the aspiration tube 3 through an interior connection means 45, with the fenestration 17 provided around walls of both tubes. Both catheters as shown in FIGS. 8a and 8b and 9a and 9b have lower area cross-sections than the embodiment shown FIGS. 7a and 7b, and may be desirable for insertion in some situations.

While the invention has been described with reference to specific embodiments, modifications and variations of the invention may be constructed without departing from the scope of the invention, which is defined in the following claims.

I claim:

1. A multiple lumen thoracostomy catheter comprises an aspiration tube with a tube wall and a proximal and a distal end for aspiring fluids from a patient from the distal end to the proximal end, an anesthetic administration tube generally of a same length as the aspiration tube being longitudinally connected to the aspiration tube wall and having a proximal end for connection to an anesthetic source for simultaneously administering anesthetic during insertion of the catheter, and a distal end for administering anesthetic to a patient along the tube wall, the connected tubes together forming a catheter having a distal insertion end and a proximal connection end, plural anesthetic administration fenestrations provided on the anesthetic administration tube along the aspiration tube wall, near the distal insertion end, and multiple aspiration apertures provided on the aspiration tube proximal the insertion end.

2. The apparatus of claim 1, further comprising the administration tube having a smaller diameter than the aspiration tube.

3. The apparatus of claim 1, further comprising both tubes being made of a flexible material.

4. The apparatus of claim 3, further comprising the materials being plastic or polyvinyl chloride material.

5. The apparatus of claim 1, further wherein each tube is made of a different material.

6. The apparatus of claim 1, wherein the plural administration fenestrations being formed as plural spaced apertures longitudinally placed on the administration tube proximal the insertion end.

7. The apparatus of claim 6, further comprising membranes provided over the fenestrations, for selective puncturing of the membranes to enable selective communication of the administration tube to given areas in the patient's body.

8. The apparatus of claim 1, further comprising the administration tube longitudinally connected to the exterior of the aspiration tube.

9. The apparatus of claim 1, further comprising the administration tube longitudinally connected within the wall of the aspiration tube.

10. The apparatus of claim 1, further comprising the administration tube longitudinally connected to the interior of the aspiration tube.

11. The apparatus of claim 1, further comprising the aspiration tube having a first aspiration opening at the insertion end, and at least one aspiration aperture in the wall of the aspiration tube proximal the insertion end for aspiring fluids at the insertion end and along a length of the inserted tube.

12. The apparatus of claim 11, wherein the aspiration aperture in the wall of the aspiration tube comprises a series of openings near the insertion end.

13. The apparatus of claim 1, further comprising the aspiration tube having a connection end for connection to an aspiration means.

14. The apparatus of claim 1, wherein the catheter further comprises an interplural aspiration catheter wherein fluids in interpleural spaces are aspired through the aspiration tube and medicants are injected to the areas surrounding the catheter through fenestrations provided in the administration tube.

15. The apparatus of claim 1, further comprising at least one administration branch tube, the branch tube incorporating application fenestrations for delivery of medicants with the administration tube.

16. The apparatus of claim 1, further comprising the administration tube having a connection end having at least one connector for receiving fluids into the administration tube.

17. An interpleural aspiration catheter apparatus comprising a first aspiration tube having a large bore longitudinally connected to a second anesthetic tube having a smaller bore, both tubes being constructed of a material suitable for catheter functions for insertion into an interpleural cavity of a patient, the first tube having an insertion end with plural aspiration openings, and having an opposite connection end for connection with aspiration means, the second tube having an insertion end with proximal plural anesthetic fenestrations extending along the first tube and communicable with the patient for administering anesthetic along a length of the catheter proximal the insertion end while inserting the catheter into the interpleural cavity.

18. The apparatus of claim 17, further comprising the fenestrations provided for administering anesthesia along a length of the second tube to alleviate discomfort to a patient.

19. A method for administering medicants to a catheterized patient comprising providing an interpleural aspiration catheter having an administration tube in longitudinal connection to an aspiration tube, providing longitudinally spaced medicant release fenestrations in the administration tube, supplying medicants to the administration tube and releasing medicants through the fenestrations along a length of the administration tube which is connected to the aspiration tube.

20. The method of claim 19, further comprising the medicants being anesthesia.

21. The method of claim 20, further comprising selectively spacing the fenestrations and selectively sedating areas of nerve concentrations.

22. The methods of claim 19, further comprising providing the fenestrations as apertures with opening sizes chosen for regulating amounts of medicants to be administered to given areas around an aperture.

23. The method of claim 20, further comprising the releasing of medicants comprising releasing anesthesia administered through fenestrations provided proximal nerve endings to selectively affect the appropriate nerve endings.

24. The apparatus of claim 19, further comprising the medicant being chemotherapy administered through fenestrations proximal diseased areas in a patient.

* * * * *